(12) United States Patent
Montenegro Rizzardini (10) Patent No.: US 7,582,318 B2
(45) Date of Patent: Sep. 1, 2009

(54) NATURAL COMPOSITION BASED ON CHILEAN MONOFLORAL HONEY EXTRACT FROM NATIVE VEGETABLE SPECIES FOR BACTERIAL INFECTION CONTROL IN VEGETABLES AT ALL

(75) Inventor: Gloria Montenegro Rizzardini, Santiago (CL)

(73) Assignees: Pontificia Universidad Catolica De Chile, Santiago (CL); Fundacion Copec-Universidad Catolica, Santiago (CL)

( * ) Notice: Subject to any disclaimer, the term of this patent is extended or adjusted under 35 U.S.C. 154(b) by 0 days.

(21) Appl. No.: 11/797,504

(22) Filed: May 3, 2007

(65) Prior Publication Data

US 2007/0275087 A1    Nov. 29, 2007

(30) Foreign Application Priority Data

May 5, 2006    (CL)    ................................. 1069-2006

(51) Int. Cl.
*A61K 36/00*    (2006.01)
*A61K 35/64*    (2006.01)
(52) U.S. Cl. ........................ 424/778; 424/725; 424/539
(58) Field of Classification Search ........................ None
See application file for complete search history.

(56) References Cited

FOREIGN PATENT DOCUMENTS

JP    2003093488 A    *    4/2003
JP    2005330285 A    *    12/2005
RU    2236248 C2    *    9/2004

OTHER PUBLICATIONS

Aljadi et al (Isolation and identification of phenolic acids in Malaysian honey with antibacterial properties, Turk J Med Sci 33 (2003) 229-236.*
Horn et al (Pollen analysis of honeys from the Los Lagos region of southern Chile (Grana 36: 160-168, 1997).*
Alissandrakis et al (Flavour compounds of Greek cotton honey, Journal of the Science of Food and Agriculture, 85: 1444-1452, 2005).*
Andrade et al (Determination of phenolic compounds in honeys with different floral origin by capillary zone electrophoresis, Food Chemistry 60 (1): 79-84, 1997).*

* cited by examiner

*Primary Examiner*—Christopher R Tate
*Assistant Examiner*—Qiuwen Mi
(74) *Attorney, Agent, or Firm*—Millen, White, Zelano, Branigan, P.C.

(57) ABSTRACT

Natural composition for controlling bacterial infections in potatoes, lettuce, vegetables, cores and flowers in general comprising extracts from monofloral honey flavonoids and/or phenols that act independently as controller of various bacterial infections.

7 Claims, 8 Drawing Sheets

NATURAL COMPOSITION BASED ON CHILEAN MONOFLORAL HONEY EXTRACT FROM NATIVE VEGETABLE SPECIES FOR BACTERIAL INFECTION CONTROL IN VEGETABLES AT ALL

The present application addresses a natural composition based on Chilean monofloral honey extract from native vegetable species for bacterial infection control in vegetables. By way of illustration, the composition of the present invention showed to be especially useful for the control of soft rot (*Erwinia* spp) in potatoes, vegetables and flowers in general.

PREVIOUS DESIGN

Bacterial diseases affect vegetable crops causing losses for agriculture. One example for this kind of diseases is the soft rot in vegetables caused by bacteria of the gender *Erwinia*. Within this bacterial gender, the species *Erwinia carotovora* pv. *carotovora* affects various crops like potatoes, artichokes, celery, sunflowers, asparagus, Brussels sprouts, cabbage, cauliflower, lettuce, eggplant, radish, turnip cabbage, melons, onions, paprika, rhubarb, tomatoes and beets. It also affects some fruit, ornamental plants like hyacinth bulbs and callas and native plants. In general, the susceptibility of plants being infected is due to the presence of an organ with abundant parenchymatic tissue, cells in which bacteria can develop due to the presence of a huge vacuole with water and other nutritive elements.

The putrescence consists in maceration and final rupture of the parenchymatic tissue of all plant organs, which finally results in death causing the ruining of the production. This is due to the action of enzymes that dissolve the middle sheet, destroying the cellular wall and impeding plasmodesmic connection, leading to an interruption in translocation of indispensable solutes for organic or plant life. On these cells starts the developing of a mucilaginous bacteria mass, of unbearable smell, typical of bacterial putrescence, hence the name of the disease.

Global losses of vegetables and flowers ascribed to soft rot add up to US$ 100,000,000 per year. (Ciampi et al., 1997). The disease can occur on fields, in gardens, in greenhouses during crop time or in the post crop phase. It can also happen during transportation and at selling places. In potato tubers (*Solanum tuberosum* L.), when conditions are favorable for the development of the disease, the total loss can add up to 75% of production, being normal ranges between 2 and 5%. It is estimated that on a field level a total of 5% is lost, whereas in stored tubers this cipher can add up to 15% (Ciampi et al., 1997) what equals to an estimated loss in Chile of 167,250 tons of potatoes, taking as a base a national production of 1,115,000 tons (source ODEPA (bureau for agrarian studies and politics) 2005).

Calla industry in New Zealand losses approximately NZ$ 2,000,000 because of this disease, what equals to 1,360,000 USD, affecting between 15-20% of stored tubers. If conditions are favorable for the disease, losses in field conditions can be total (Vanneste, 1997) for this reason currently only the in vitro propagation is used on a commercial level; this makes crop production more expensive. (personal communication, PIGA Seed S.A. Manager, 2005).

Currently there are serious problems for controlling these pathogens due to the lack of commercial bactericides; farmers just throw away vegetable products with putrescence.

Control measures are preventive, like: the use of healthy tubers, certified seeds, resistant cultures, perform rotation with non lodging crops, throw way sick plants, use soils with good draining and manage the relative humidity in storage Eradication of the pathogen is difficult and in experimental field conditions no good control levels have been shown. Literature mentions the use of formaldehyde, sodium hypochlorite, citric acid and some bactericide formulations like Strepto Plus (gentamicyne sulphate with oxytetracycline chlorohydrate) utilizing a dose between 60-120 g/HL. Another not so often used product because of dyeing the eatable organ blue is copper oxychloride.

On the other hand, controlling these bacteria becomes complicated as the different bacterial subspecies of the complex *Erwinia carotovera* can cause soft rot and black leg depending on the conditions of the environment where the plants are cropped. Furthermore, the latent infection risk in tuber-seeds allows the appreciation of disease symptoms only once the crop has been established. Another related actor is that pathogens frequently are protected within the lenticels or vascular system and therefore are not affected by the usually used commercial disinfectants.

Within the area of control with organic based products we can mention the possibility of using a product coming from citric fruit extracts (CITRUPAR 80) acting as a "natural antibiotic" for the control of these pathogens.

It is important to mention that the existence of extracts from vegetable origin is appreciated; as for example the one disclosed in the Chilean invention patent applications 2886-2001 (US Application Pub. No. 2004/0052878) and 2377-2004 (US Application Pub. No. 2006/0210660), insecticides as well as acaricides, and agents from the active substances Hederacocido and Alfa-Hederina. Also observed is the patent application 67-1999 (U.S. Pat. No. 6,623,767 B1) that comprises honey combined with other ingredients, useful as cosmetics and for sanitary disinfections.

On the other hand, the Russian patent application RU2236248 dated $27^{th}$ Dec. 2001 and published on $20^{th}$ Sep. 2004, discloses an immunotropic preparation for medical and pharmaceutical use where a preparation based on honey obtained from bees fed with a composition that comprises honey obtained from one sole flower extracted from the plant family Compositae and that comprehends specific flavonoids to include the synthesis of interferona Alfa and Beta, presenting high effectiveness in the treatment of viral and bacterial prophylaxis. Similar compositions can be observed in the Russian applications RU2236247 and RU2236244.

However, none of the publications of the previous design resolve the problem of bacterial infections suffered by vegetables as described previously. As described, one of the most affected crops by these bacteria is the potato. (*Solanum tuberosum* L.). Therefore, the use of a toxic compound is not feasible, as it wouldn't allow consumption of the tuber. In spite of the good results obtained in vitro using chemicals for controlling *Erwinia* spp. it hasn't been effective as a method for disinfecting tubers.

In the specific case of controlling soft rot in potato tubers, products like streptoplus (sulphate) have been used, sodium benzoate and chlorine dioxide, o-phenylphenate, experimental bactericides like CGA 78039, sodium hypochlorite and citric acid in 1%, formaldehyde, followed by drying with blast.

As most of the horticultural products affected with putrescence by *Erwinia* are consumed as food, for the control of this rot no synthetic products derived from antibiotics that can have toxic effects on the human species can be used. Furthermore, globalization nowadays doesn't allow us the use of antibiotics, as the major part of the international market corresponds to countries with barriers regarding products derived from antibiotics for controlling this type of bacterial diseases.

The solution of the invention solves the previously described problems by a product based on monofloral honeys corresponding to an innocuous organic compound whose "raw material is unique to the world" as the botanic origin of the honey to be used indicate that it only can be produced in Chile. This allows the antibiotic soft rot controlling product to be produced in Chile and to benefit the control of bacteria in potatoes, vegetables and fruit by means of a natural product that doesn't harm the qualities of the species applied on and fulfilling all international norms with regards to this matter. On the other hand, it offers a big opportunity for the national apicultural sector in general.

To sum up, the advantages or benefits of the invention's object are as follows:

100% natural product Non-toxic to humans and animals
Wide spectrum germicide, of rapid action and very effective against *Erwinia carotovora* pv. *Carotovora*
It doesn't irritate skin or eyes of humans or animals and it is inoffensive to the mucous membrane.
It has conservation properties, that is, bacteriostatics.
Optimal stability in ph 2 to 12 and temperatures up to 130° C.
It isn't volatile.
It is "selective".
It is no antibiotic, but it works in a similar way.
It is compatible with antibiotics, sulphates etc.

BRIEF DESCRIPTION OF THE FIGURES

FIG. 7—ELISA plate with *P. syringae* pv. *Syringae*. The first three lines correspond to in vitro growth of the bacteria in environments with M349 extract and soy medium. The bacteria growth can be appreciated from the fourth column on.

DETAILED DESCRIPTION OF THE INVENTION

The invention corresponds essentially to a composition obtained from extract of flavonoids and/or phenols of monofloral honey, preferably Chilean honey derived from different species and who act independently as controllers for different bacterial infections in various vegetable species.

The botanic origin of each honey is determined through a separation process of the pollen grains by centrifugation and its posterior staining and observation under a light microscope. Data was quantified statistically. With this method honey is considered monofloral when more than 50% of the pollen present in the honey correspond to one sole vegetable species.

To perform honey extraction, and only for illustrative means as an experienced medium-level technician could clearly extrapolate the following mentioned quantities, a process is carried out that contains the following phases:

1. 50 gr honey is weighed
2. This is dissolved with 100 ml distilled water acidified with HCl (pH=2).
3. The solution is put into a volumetric flask of 250 ml and it is filled to said volume with acid water.
4. The solution is filtered with cotton and passed through a column of Amberlite XAD-2 resin (250 mm height by 20 mm de diameter), at a dropping speed of 2 ml/min. Phenolic compounds will be retained in the column.
5. The column is cleaned with 100 ml acid water. The liquid is thrown away.
6. It is washed a second time with 200 ml neutral distilled water. The liquid is thrown away.
7. It is washed a third time with 300 ml pure methanol. Methanol will separate the phenolic compounds of the column. Methanol is recollected in a clean glass or flake and it is passed to a balloon for 500 ml rotoevaporator.
8. The methanolic solution concentrates until dryness in the rotoevaporator at 45° C. (approximated time: 12 hrs at high rotation speed).
9. The residue is re-suspended in 5 ml distilled water.
10. The suspension is put in a funnel for decantation, and 5 ml diethylic ether. The ethereal phase is collected (lower coloured phase), and it is extracted again twice with 5 ml ether.
11. The ethereal solution concentrates until dryness in the rotoevaporator at 45° C. (approximated time: 1 hrs at high rotation speed).
12. The residue is re-suspended in 2 ml sterilized distilled water with autoclave at 15 pound pressure (125° C.) for 15 minutes, afterwards the extract is filtered through syringe filters of 0.45 um (pore size) and it is stored at −20° C.

The before described process made it possible to obtain monofloral honey extracts with what different tests were performed for the control of bacterial soft rot in potato tubers in general.

A chromatographic analysis to analyze the phenolic and flavonoid compounds present in the honey allowed to determine that the present compounds in the extract correspond to galic acid, cumaric acid, pherulic acid, salicylic acid, naringenine and kaempherol.

In spite of the procedure described above it is also possible to obtain ethanolic honey extracts. To this end, in point 4 of the process, part of the diluted honey is collected and filtered with 0.45 um filters and stored at −20° C. In point 9 of the process the residue is re-suspended in 85° ethylic alcohol then it is filtered with 0.45 um filters and stored at −20° C. In point 12 of the process the residue is re-suspended in 85° ethylic alcohol then it is filtered with 0.45 um filters and stored at −20° C.

This procedure allowed obtaining an innocuous and organic honey product of simple elaboration and compatible with integrated plague and disease management. As it is an innocuous product it can be used in conventional and organic agriculture. Afterwards the extract can be formulated in different ways, like for example and not limiting to, dissolution in distilled water that can be presented in a spray product (atomization) or as a bactericide solution.

When applying the product, its action mode is due to compounds with floral origin that are not peroxidic, acting by inhibiting the bacterial development with a bacteriostatic action on the pathogen. That is, it is a product for contact.

Application method for its use in bacterial development inhibition in vegetables is given by solutions that contemplate a dose higher than 10% of the extract. Notwithstanding, studies have been performed with other formulations and results have been also successful.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and, all parts and percentages are by weight, unless otherwise indicated.

The following examples show the efficiency in disease control and development inhibition of *Erwinia carotovora* pv. *Carotovora*, by extending the post-crop time for vegetable products and lowering the associated losses.

EXAMPLE 1

In situ and in vitro Growth Inhibition of the Bacteria *Erwinia carotovora* pv. *carotovora*, a Bacteria that Causes Black Leg and Soft Rot of Potato Tubers (*Solanum tuberosum* L.)

In the experimental study performed to show the efficiency of the product presented in this patent application, the in vitro and in situ inhibition of growth of the *Erwinia carotovora* pv. *carotovora* bacteria, that causes black leg and humid rot of potatoes (*Solanum tuberosum*) was observed, through the effect of solutions obtained out of 3 monofloral Ulmo honeys (*Eucryphya cordifolia*), dominant native species of the Bosque Templado in southern Chile.

The culture medium used for bacteria growth was B de King (KB). The inoculum used was bacterial isolation coming from commercial potato tubers from the region of San Fernando. Afterwards a biochemical battery was used to determine the bacteria and the stump plus the gram-staining, resulting in the stump *Erwinia carotovora* pv. *carotovora* (Ecc). The in vitro bacterial growth inhibition analysis was based on the quantification of bacterial growth inhibition halo measuring the inhibition area with a planimeter, the MIC (minimum inhibition concentration) of each honey was also measured and the technique of agar diffusion was used (well diffusion agar) adding honey into the culture medium to different volumes observing the bacterial growth. Concentrations between $10^5$ to $10^7$ UFC (colony forming units/ml) were used. Statistic analysis was based on a completely random design with ANDEVA and TURKEY-Kramer statistic analysis to 95-5 confidence each. On the other hand, honeys were analyzed with a pH 4 adjusted sugared solution that contained in an average proportion the most important sugars present in honeys.

Afterwards an analysis of the in situ activity of monofloral Ulmo honeys was performed. The inhibition of bacterial growth in potato tubers of the variety Desireé (principal potato in the Chilean market) was analyzed in two ways: 1) Inoculating through a 0.5 ml syringe with bacterial solution and distilled water with a concentration of $10^7$ UFC and putting on the inside of the tuber honey solutions in different concentrations with an other syringe. 2) Inoculating through a 0.5 ml syringe with bacterial solution and distilled water with a concentration of $10^7$ UFC and brushing the outside of the tuber with different honey solutions.

The honeys that showed highest bactericide activity against Ecc were the honeys coded as M182, M84 and M335 whose botanic origins can be observed in the figures that complete the present description.

Result of the Effect of Honey M182 and M84 on Bacteria Ecc Colonies

The organic and innocuous honeys were prepared in different aqueous solutions that corresponded to: 1:10; 1:4; 1:1 (v/v). All solutions showed inhibition, however the concentration to 50% had the highest data. Results showed the inhibition of the bacterial growth in a range of from 40 to 80% in dose 1:10 v/v of honey and distilled water in potato tubers with a bacterial dose of ($3.7 \times 10^7$ UFC). The number of experimented samples showed significant differences of inhibition in relation to control.

FIG. 1 shows the high impact the application of the product based on monofloral honeys had on the infected sample. Said graphic shows that a 50% of concentration v/v had a high control percentage in the incidence of soft rot.

As to honey M335, whose botanic origin can be observed in FIG. 4, it is possible to deduce significant results in its application. This honey was tested in dissolutions of 10% v/v. It showed a 60% in vitro bacterial growth inhibition comparing to sugar and ph 4 adjusted solutions, present in average in honeys (fructose 38.5% (w/w), glucose 31%, 7.2% maltose, 1.5% sucrose) (D'Arcy, 2001. Data USDA), solution that didn't give or showed to be less effective for inhibition in vitro of *Erwinia carotovora* pv. *Carotovora*.

Honey M335 corresponded to an extract of flavonoids derived from organic monofloral ulmo honey that controls bacterial soft rot of potato tubers post crop. Its composition is as follows:

| Compound | Concentration (ug/mL) |
|---|---|
| Galic acid | 0.236 ∓ 0.005 ug/ml |
| Cumaric acid | 0.221 ∓ 0.005 ug/ml |
| Pherulic acid | 0.235 ∓ 0.005 ug/ml |
| Salicylic acid | 0.435 ∓ 0.005 ug/ml |
| Naringenine | 0.456 ∓ 0.005 ug/ml |
| Kaempherol | 0.174 ∓ 0.005 ug/ml | pH: 4.9 a 5.5

EXAMPLE 2

In vitro and in situ Growth Inhibition of Bacteria *Erwinia carotovora* pv. *carotovora*, in Seed Tubers of Five Potato Varieties (Desiree, Cardinal, Atlantic, Karu-INIA and Pukara-INIA) in Storage Conditions For evaluating the effectiveness of the described invention on bacterial soft rot the following study was performed using seed tubers of five different potato varieties (Desiree, Cardinal, Atlantic, Karu-INIA and Pukara-INIA), putting them under storage conditions. The following treatments were used: 1 Healthy sample 2. Inoculated with *Erwinia carotovora* pv. *carotovora,* 3. Inoculated with *Erwinia carotovora* pv. *carotovora* plus application of honey M349 extract, 4. Inoculated with *Erwinia carotovora* pv. *Carotovora*, plus application of the product Citrupar-80.

The procedure or preparing the honey extract as well as the preparation of the inoculums and the inoculation of the five potato varieties corresponded to the same protocol described in example 1.

Afterwards the tubers were distributed in plastic boxes with a completely random factorial design to be put in storage, in darkness and covered with Rachel mesh, and they were analyzed after 50 days.

Severity was evaluated cutting the core of each tuber in length, using the Horsfall-Barrat (1945) scale that considers area percentage of the tuber with putrescence according to the following scale:

| Grade | Percentage |
|---|---|
| 1 | 0% |
| 2 | 1-3% |
| 3 | 3-6% |
| 4 | 6-12% |
| 5 | 12-25% |
| 6 | 25-50% |
| 7 | 50-75% |
| 8 | 75-87% |
| 9 | 87-93% |
| 10 | 93-96% |
| 11 | 96-99% |
| 12 | 100% |

Evaluation data was submitted to statistic analysis (Andeva), separation occurred according to the DMS test ($p<0.05$).

Prior to Andeva the data of the variable incidence transformed to square root of % plus 0.5

CHART 1

Soft rot severity comparison between different treatments with diverse potato varieties in storage conditions, La Platina, 2006. Averages with the same letter, in the same column, do not differ among each other, according to test DMS ($p < 0.05$)

| | VARIETIES | | | | |
|---|---|---|---|---|---|
| Treatments | Atlantic | Cardinal | Desiree | Karu-INIA | Pukara-INIA |
| Control (+): sample without inoculation | 1.76 b[1] | 1.06 d | 1.06 b | 1.15 d | 1.03 c |
| Control (−): sample inoculated with Ecc | 2.41 a | 1.7 a | 1.18 b | 1.46 a | 1.26 b |
| Inoculated plus "organic product" | 1.31 c | 1.38 c | 1.85 a | 1.5 a | 1.65 a |
| Inoculated plus Citrupar-80 | 2.38 a | 1.56 b | 1.00 b | 1.3 b | 1.18 b |

[1]different letters correspond to different statistics among varieties, the average values of severity are expressed according to Horsfall-Barrat scale The results obtained in this essay allowed concluding the evaluation of severity in which interaction was found among the varieties through the described statistic parameters. The product had a good effect in reducing soft rot damage in the varieties Atlantic and Cardinal. (Chart 1)

EXAMPLE 3

In vitro and in situ Growth Inhibition of the Bacteria *Erwinia carotovora* pv. *carotovora*, in Lettuce Type Great Lakes with Honey M349 Extract In order to evaluate growth of the bacteria *Erwinia carotovora* pv. *carotovora* lettuce type Great Lakes (n=18) was used distributed in 4 treatments: healthy sample, infected sample, lettuce treated with M349 extract and infected lettuce treated with M349 extract in a solution of 10% v/v. Artificial infection of the lettuce was carried out with a dripping atomizer covering the total surface of each infected lettuce. Afterwards the treatments were sprinkled. Each lettuce was packed in transparent bags and put under greenhouse conditions at 30° C. for seven days.

Severity was evaluated cutting the core of each tuber in length, using the Horsfall-Barrat (1945) scale that considers area percentage of the tuber with putrescence according to the following scale:

| Grade | Percentage |
|---|---|
| 1 | 0% |
| 2 | 1-3% |
| 3 | 3-6% |
| 4 | 6-12% |
| 5 | 12-25% |
| 6 | 25-50% |
| 7 | 50-75% |
| 8 | 75-87% |
| 9 | 87-93% |
| 10 | 93-96% |
| 11 | 96-99% |
| 12 | 100% |

Evaluation data was submitted to statistic analysis (Andeva), separation occurred according to the DMS test ($p<0.05$).

Prior to Andeva the data of the variable incidence transformed to square root of % plus 0.5

CHART 2

Soft rot severity comparison between different treatments in lettuce variety Great Lakes (n = 20) in storage conditions, PUC, 2007.

| Treatment | Putrescence severity expressed in Horsfall-Barrat scale |
|---|---|
| Healthy sample | 2.0 ± 2.0 a[1] |
| Not infected lettuce treated with M349 extract | 2.6 ± 2.3$^a$ |
| Infected lettuce treated with M349 extract | 3.2 ± 2.2$^a$ |
| Infected sample | 7.4 ± 1.3$^b$ |

[1]Averages with the same letter do not differ among each other, according to test DMS ($p < 0.05$)

7 days later the infected lettuce treated with M349 extract didn't show any significant changes as to the presence of the disease compared to healthy samples and lettuce treated with M349 extract, obtaining soft rot levels in those treatments between 1 and 6% of affected area with disease, on the other hand the statistically different lettuce group corresponded to treatment of infected sample where the reached putrescence levels are close to 80% of putrescence.

Figure 1:
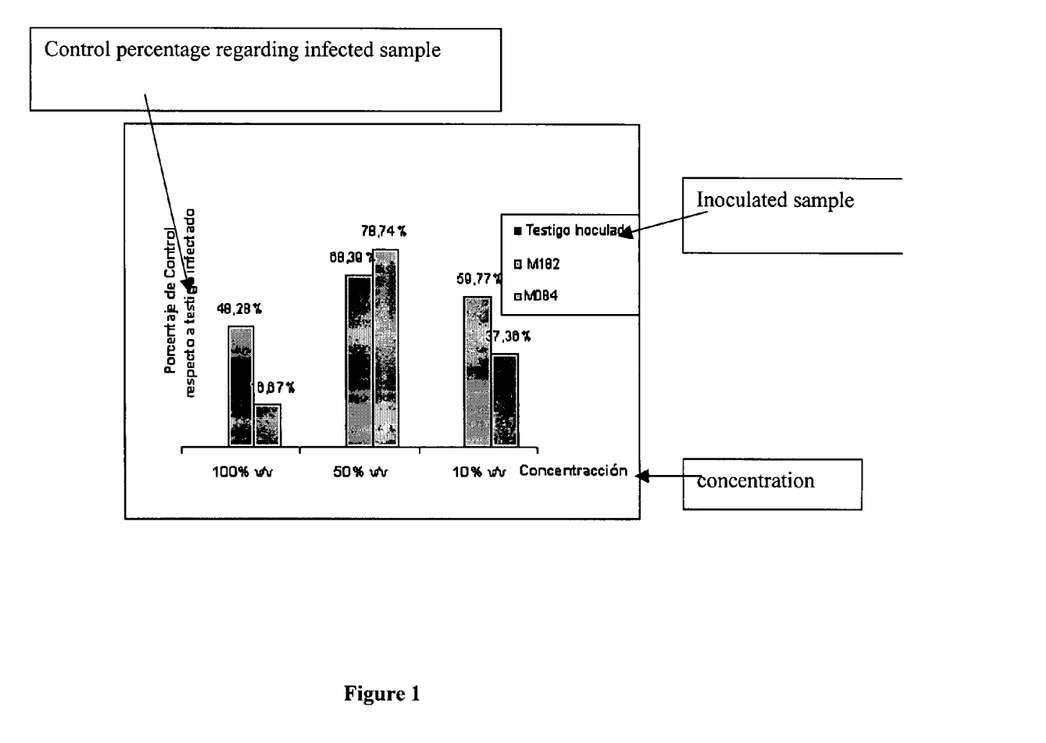
FIG. 1: Corresponds to a graphic showing the incidence of soft rot in potato tubers of the variety Desireé treated with monofloral honey in post crop conditions.
Figure 2:
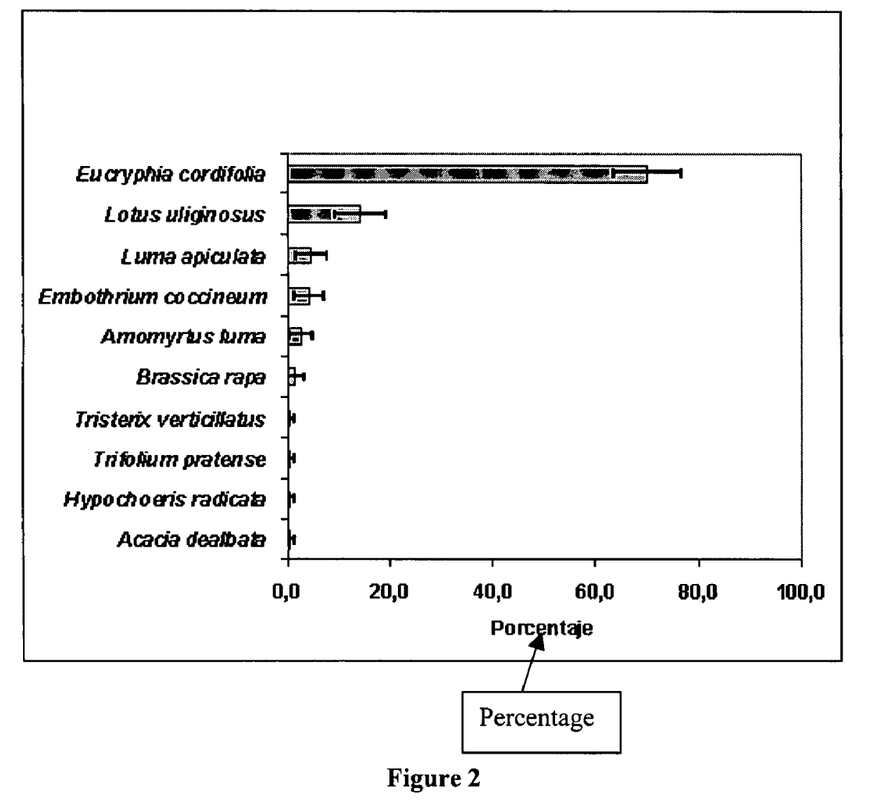
FIG. 2: Corresponds to a graphic showing the botanical origin of one of the tried honeys, M182, to exemplify the invention.
Figure 3:
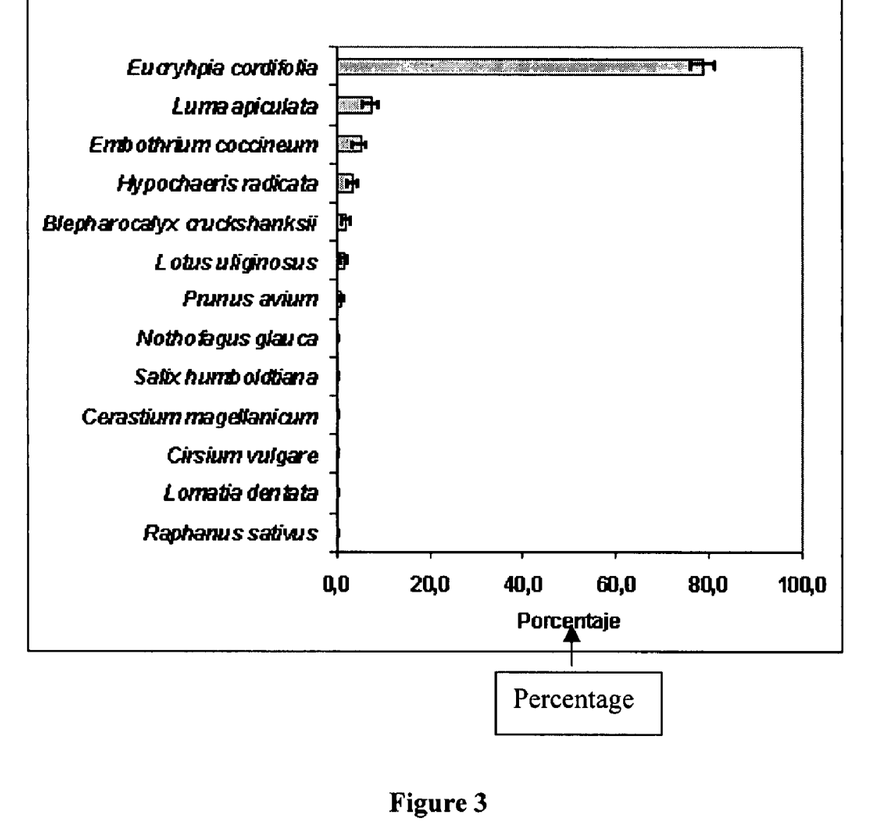
FIG. 3: Corresponds to a graphic showing the botanical origin of one of the tried honeys, M84, to exemplify the invention. This honey represents a monofloral Ulmo honey, as the frequency of the Ulmo pollen grains found was over 50%.
Figure 4:
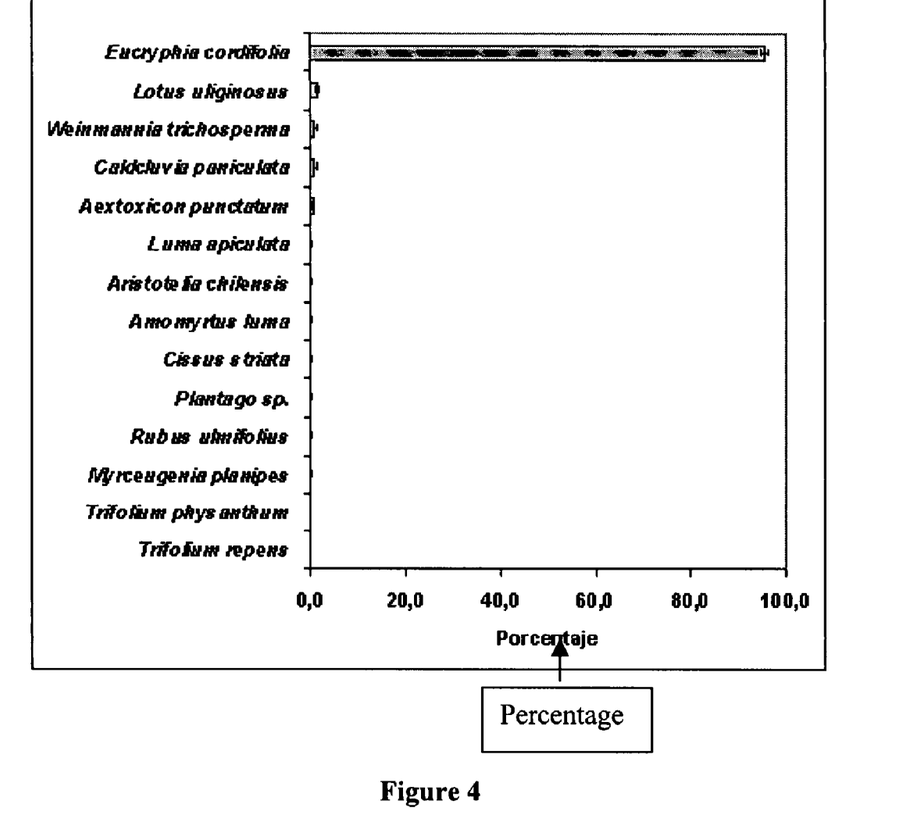
FIG. 4: Corresponds to a graphic showing the botanical origin of one of the tried honeys, M335, to exemplify the invention.
Figure 5:
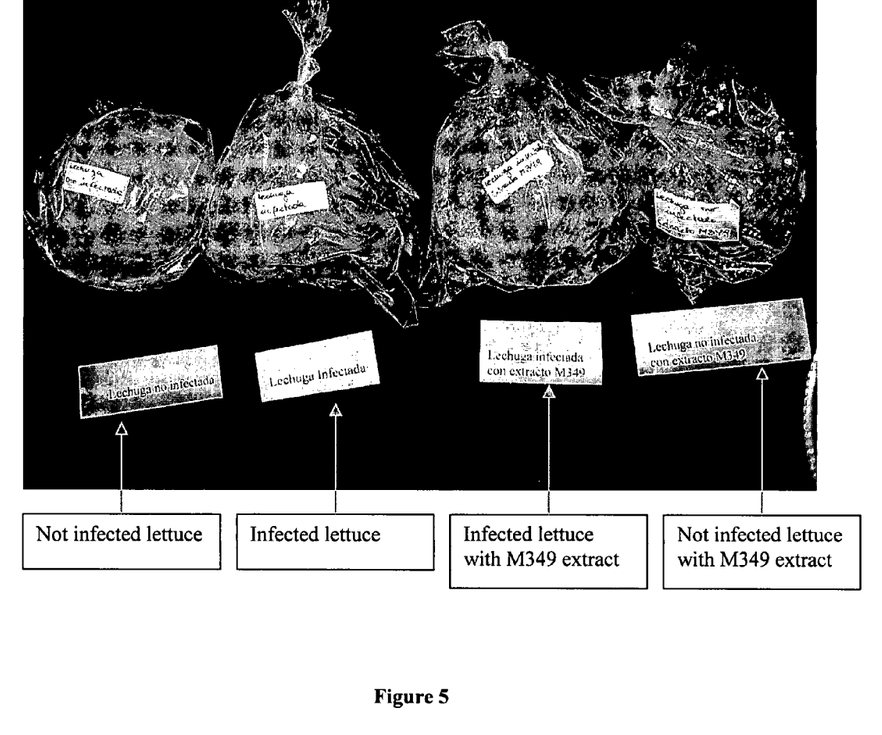
FIG. 5—corresponds to example 3 where visual differences of soft rot in lettuce type Great Lakes can be appreciated. From left to right you can see not infected lettuce, infected lettuce, infected lettuce treated with M349 extract and not infected lettuce treated with M349 extract.

The treatment in lettuce infected and treated with M349 extract controlled the disease in this evaluation period that was observed with putrescence corresponded to sick sample. (Image 5)

EXAMPLE 4

Figure 6:
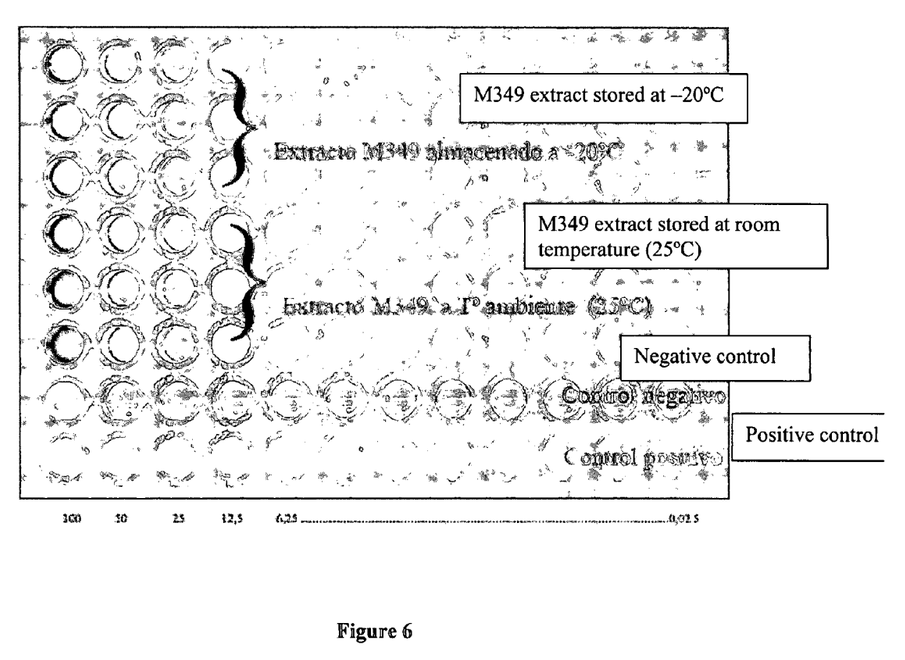
FIG. 6—ELISA plate where you can observe the in vitro growth inhibition of *Erwinia carotovora* pv. *carotovora* with M349 honey extract.

Evaluation of the Bacteriostatic Activity of the Aqueous Honey Extract M349 Stored in Different Storage Conditions The bacteriostatic activity of the aqueous honey extract M349 stored for 30 days at room temperature and at −20° C., was evaluated about the growth control in vitro of *Erwinia carotovora* pv. *carotovora*, determining the minimum concentration of the extract able to inhibit the bacterial growth (image 6)

From the obtained results we can observe that the M349 extract stored at 25° C. inhibited the in vitro growth of *Erwinia carotovora* pv. *carotovora* at concentrations higher than 0.188 μl of extract/μl of solution. On the other hand the M349 extract stored at −20° C. inhibited the in vitro growth of *Erwinia carotovora* pv. *carotovora* at concentrations higher than 0.188 μl of extract/μl of solution.

The results show that the activity of the honey extract presented in the patent application is able to go on inhibiting the growth of the bacteria causing Soft Rot even under storage conditions in shelves at room temperature (25° C.) and storage at low temperatures.

No significant differences of the bacteriostatic activity were found between these two extracts stored under different storage conditions, the temperature didn't affect the bacteriostatic activity of the extract.

EXAMPLE 5

Evaluation of the Bacteriostatic Activity of the Aqueous Honey Extract M349 on *Pseudomonas syringae* pv. *syringae*, Agent that Causes Bacterial Cancer of Cores (Apricots, Plums, Cherries, Almonds, Peaches)

*Pseudomonas syringae* pv. *syringae* is a Gram negative bacteria, that causes the disease called bacterial cancer, that attacks fruit trees like: mazzard, almond tree, cherry-tree, apricot tree, peach tree, pear tree and some crops like rice. It affects young and adult trees unleashing a series of symptoms (syndrome). Among the most important damages we find the not uniform and retarded sprout, acid sap, and exudation of gum. However, an uncontrolled or bigger attack is able to generate death of mother branches, buds, flowers and even the entire tree (FIG. 7). *Ps. syringae* pv *syringae* on his part is able to affect the fruits, provoking a brown leisure with an aqueous margin that impedes its commercialization. All these damages are because of the bacteria producing syringomicine fitotoxin, which consist in a greasy acid of variable length linked to a cyclic peptide.

The ways of dissemination of the bacteria are various, being the main one eluviation by rain and penetration by prune wounds.

Disease control is allotted to cultural measures, like for example, not to prune with wet wood, or to disinfect the scissors and saws, and the elimination of affected branches (who, as last solution, are burnt). For this reason the search for efficient products that ensure a good control of the disease and are also environmental friendly (from its production to its discard) is preferential for national agro industry. On account of this, there is currently a huge interest in studying antimicrobial properties of plant extracts and other products that can ensure a good control of this and other diseases with similar characteristics.

Figure 7:
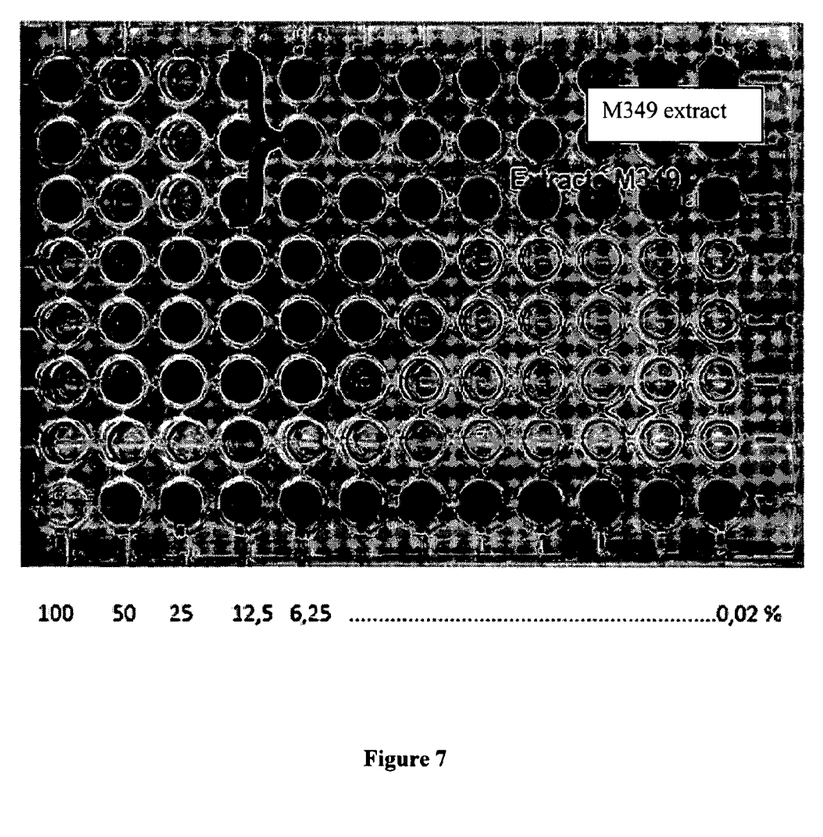

The activity of the honey extract M349 was evaluated through determining the minimum concentration of the extract able to inhibit bacterial growth in ELISA plates (FIG. 7).

The extract M349, inhibited in vitro growth of *Pseudomonas syringae* pv. *syringae* in concentrations higher than 0.188 ul of extract/μl DE ul of solution.

The extract M349 in vitro, shows a promising activity on the agent causing bacterial cancer in cores, with a potential use as biocontroler of the disease.

EXAMPLE 6

Evaluation of Bacteriostatic Activity in vitro of Extract M349 on Human Pathogens The analyzed bacteria species and their stump belonged to:
1. *Enterobacter aerogenes* Hormaeche and Edwards ATCC 13048, enteric bacteria causing intrahospitalarian gastrointestinal disorders.
2. *Escherichia coli* (Migula) ATCC 25922, bacteria of enteroagregative type (ECEAgg) able to survive long time in human intestine, producing through toxins diarrhea in a severe infection.
3. *Pseudomonas aeruginosa* (Schroeter) Migula ATCC 27853. Causing skin infections associated mainly to its presence in nosocomial infections (intrahospitalarian)
4. *Salmonella typhi* STH 2370 Causing typhoid fever, like other enteric pathogens, infection by *S. typhi* are transmitted by food and water contaminated by human feces with acute infection, persistent excretors or asymptomatic chronically carriers. Humans are the only host of *S. typhi*; there are no environmental reservoirs.
5. *Vibrio cholerae* ISP, causing cholera, acute associated gastrointestinal disease.
6. *Staphylococcus aureus* subsp. *aureus* Rosenbach ATCC 25923, bacteria found on skin and nasal cavities of healthy people, causing huge variety of diseases, from minor infections to the skin (furuncles, blister, bladders) and cutaneous abscesses up to diseases that can endanger life like pneumonia, meningitis, endocarditis, toxic shock syndrome (TSS) and sepsis.
7. *Streptococcus pneumoniae* type B common agent of low and high respiratory diseases, like pneumonia and medium acute earache (infections to the middle ear), and meningitis, that affect children and adults globally.

The activity of the honey extract M349 was evaluated determining the minimum concentration of the extract capable to inhibit bacterial growth on ELISA plates with microbiology technique of microdilution in elisa plates with 96 wells (Broth microdilution methods) (Chart 3).

CHART 3

Minimum concentration of in vitro inhibition of bacterial growth of human pathogens of extract M 349.

| Bacteria | MIC (μl of extract/μl of solution |
|---|---|
| *Enterobacter aerogenes* | 0.188 |
| *Escherichia coli* | 0.188 |
| *Pseudomonas aeruginosa* | 0.188 |
| *Salmonella typhi* | 0.188 |
| *Vibrio cholerae* | 0.047 |

CHART 3-continued

Minimum concentration of in vitro inhibition of bacterial growth of human pathogens of extract M 349.

| Bacteria | MIC (µl of extract/µl of solution) |
|---|---|
| Staphylococcus aureus | 0.188 |
| Streptococcus pneumoniae type B | 0.047 |

The extract percentage column was eliminated as it is explained in the MIC column.

The honey extract M349 inhibited the in vitro growth of all bacteria, distinguishing two groups according to the minimum concentration of inhibition (MIC) of the extract.

For bacteria: *Enterobacter aerogenes, Escherichia coli, Pseudomonas aeruginosa, Salmonella typhi, Staphylococcus aureus*, the obtained MIC was 0.188 µl of extract/µl of solution Extract M349, inhibited in vitro growth to a minor concentration of the bacteria *Vibrio cholerae* and *Streptococcus pneumoniae* type B with an obtained MIC of 0.047 µl of extract/µl of solution.

EXAMPLE 7

Cellular Toxicity Evaluations of Extract M349

Rat spermatozoids were used (Balb-c), these cells are considered the most sensitive for this kind of evaluation. Spermatozoids were cultured in a medium completing with different concentrations of the honey extract M349 (1:10, 1:100, 1:1000, 1:10000 v/v)

The cellular viability of the spermatozoids was evaluated at different time intervals (t=0 hr, t=1 hr, t=2 hrs, t=4 hrs), approx 100 spermatozoids were observed in each interval and the percentage of spermatozoids presenting motility, parameter for cellular viability, was obtained. (FIG. 8)

Figure 8:
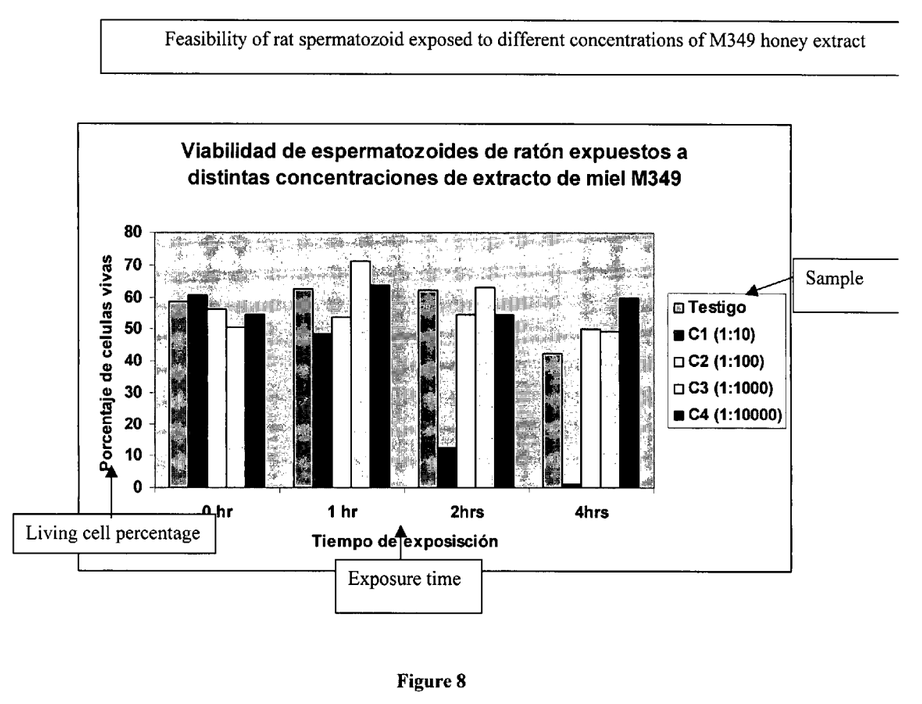
FIG. 8—feasibility of rat spermatozoids exposed to different concentrations of M349 honey extract expressed in percentage of living rat spermatozoids (n=100) and observation time.

FIG. 8 shows that besides the concentration 1:10 (high dose to determine toxicity), about 50% of the spermatozoids are observed active after 4 hours of observation. Furthermore, after 4 hours, the number of observed living spermatozoids is equal or superior to the one observed in the middle of the control to the concentrations C4 (1:10000), C3 (1:1000) y C2 (1:100), this result is interpreted as a very low or almost non toxicity of the extract on these cells.

The entire disclosures of all applications, patents and publications, cited herein and of corresponding Chilean application No. 1069-2006, filed May 5, 2006, and is incorporated by reference herein.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. An extract comprising flavonoids and/or phenols from monofloral ulmo honey (*Eucryphia cordifolia*), said extract comprising gallic acid in the amount of 0.236±0.005 µg/ml, coumaric acid in the amount of 0.221±0.005 µg/ml, pherulic acid in the amount of 0.235±0.005 µg/ml, salicylic acid in the amount of 0.435±0.005 µg/ml, naringenin in the amount of 0.456±0.005 µg/ml and kaempherol in the amount of 0.174±0.005 µg/ml, with a pH: 4.9 to 5.5, wherein said extract is prepared by a process comprising:
   a) weighing a quantity of honey;
   b) diluting said honey in distilled water acidified with HCl (pH=2) to form a solution;
   c) putting the solution in a volumetric flask and filling the flask up with additional acid water;
   d) filtering said solution obtained in step c) and passing it through a column of cationic exchange at a constant dropping speed for phenolic compounds to be retained in said column;
   e) cleaning said column with acid water and discarding the acid water that passes through the column;
   f) cleaning said column a second time with neutral distilled water and discarding the neutral distilled water that passes through the column;
   g) cleaning for a third time with pure methanol to elute the phenolic compounds from the column, gathering methanol elute, and rotoevaporating the methanol elute to vacuum dryness at a temperature of 45° C., in order to eliminate the methanol and concentrate the obtained phenolic compounds to form a residue in a rotoevaporator;
   h) re-suspending the residue in distilled water to form a suspension;
   i) extracting the suspension 3 times with diethyl ether to form a diethyl ether extraction solution;
   j) concentrating said diethyl ether extraction solution to dryness in a rotoevaporator to form a second residue;
   k) re-suspending the second residue in sterilized distilled water;
   l) filtering the resuspended residue through a nitrocellulose syringe filter of 20 µm and storing the filtered residue at −20° C.

2. A method of preparing the monofloral ulmo homey extract of claim 1 comprising:
   a) weighing a quantity of honey;
   b) diluting said honey in distilled water acidified with HCl (pH=2) to form a solution;
   c) putting the solution in a volumetric flask and filling the flask up with additional acid water;
   d) filtering said solution obtained in step c) and passing it through a column of cationic exchange at a constant dropping speed for phenolic compounds to be retained in said column;
   e) cleaning said column with acid water and discarding the acid water that passes through the column;
   f) cleaning said column a second time with neutral distilled water and discarding the neutral distilled water that passes through the column;
   g) cleaning for a third time with pure methanol to elute the phenolic compounds from the column, gathering methanol elute, and rotoevaporating the methanol elute to vacuum dryness at a temperature of 45° C., in order to eliminate the methanol and concentrate the obtained phenolic compounds to form a residue in a rotoevaporator;
   h) re-suspending the residue in distilled water to form a suspension;
   i) extracting the suspension 3 times with diethyl ether to form a diethyl ether extraction solution;
   j) concentrating said diethyl ether extraction solution to dryness in a rotoevaporator to form a second residue;
   k) re-suspending the second residue in sterilized distilled water;

l) filtering the resuspended residue through a nitrocellulose syringe filter of 20 μm and storing the filtered residue at −20° C.

3. The method according to claim 2, wherein the filtering process in step d) is performed with hydrophobe cotton or Watman filter paper No. 2; the column is resin Amberlita XAD-2; and the dropping speed is in the range of 2±0.2 ml per minute.

4. A method for controlling bacterial infections in potatoes, lettuce, vegetables, and flowers comprising administering thereto the extract according to claim 1.

5. A method according to claim 4, comprising controlling the growth of bacteria *Erwinia carotovora* pv. *Carotovora*, which causes black leg and soft rot in potato.

6. A composition for controlling bacterial infections, comprising the extract according to claim 1, formulated based on a dissolution in water as a spray product for atomization or as a bactericide solution.

7. A composition for controlling bacterial infections according to claim 6 wherein said composition comprises at least 10% v/v of monofloral ulmo honey extract.

* * * * *